United States Patent [19]

Van Pool

[11] Patent Number: 4,513,165

[45] Date of Patent: Apr. 23, 1985

[54] ALKYLATION PROCESS

[76] Inventor: Joe Van Pool, c/o Ste. 1107, 1825 K St., NW., Washington, D.C. 20006

[21] Appl. No.: 620,787

[22] Filed: Jun. 15, 1984

[51] Int. Cl.³ .............................................. C07C 2/58
[52] U.S. Cl. .................................... 585/723; 585/719
[58] Field of Search ............................... 585/719, 723

[56] References Cited

U.S. PATENT DOCUMENTS

| | | | |
|---|---|---|---|
| 2,372,338 | 6/1942 | Penisten | 260/683.4 |
| 3,579,603 | 5/1971 | Jones | 260/683.48 |
| 3,721,720 | 3/1973 | Chapman et al. | 260/683.48 |
| 3,993,706 | 11/1976 | Mikulica et al. | 260/683.48 |
| 4,236,036 | 11/1980 | Dixon et al. | 585/723 |
| 4,239,931 | 12/1980 | Mikulica | 585/723 |
| 4,373,110 | 2/1983 | Hutson | 585/723 |
| 4,404,418 | 9/1983 | Hutson et al. | 585/723 |

*Primary Examiner*—Curtis R. Davis

[57] ABSTRACT

A slip stream of system HF from HF alkylation is charged to propane stripping of the fractionation system to purify the HF for recycle to the alkylation. Bottoms yield from propane stripping is fractionated to separate propane from the acid soluble oil separated from the slip stream of HF.

10 Claims, 1 Drawing Figure

ALKYLATION PROCESS

This invention relates to catalytic alkylation process. It particularly relates to a process for producing high octane alkylated hydrocarbons. It specifically relates to an improved process for the alkylation of isoparaffins with olefins and to a modified acid catalyst regeneration system.

It is well known in the prior art that catalyst alkylation utilizing sulfuric acid or hydrofluoric acid as catalysts is an important chemical tool for preparing alkylated hydrocarbons and derivatives thereof. It is essential for commercial acceptability that HF catalysts utilized in alkylation processes exhibit a prolonged capability for performing its intended function as well as a high degree of activity in performing its intended function as well as a high degree of activity in effecting such function. Catalyst regenerating equipment is commonly provided in HF alkylation units to periodically remove contaminants from the catalyst in order to maintain activity.

This invention relates to safe disposal of HF acid soluble oils (ASO), which are produced as an undesirable by-product in the HF catalytic alkylation of an isoparaffin, usually isobutane, with an olefin, usually at least one of propylene, butene-1, butenes-2, and isobutylene. The ASO builds up in the operation and is usually recovered from the system by means of an HF rerun column to which a slip stream of system HF catalyst is charged with HF and isobutane being removed overhead from the rerun column and returned to the alkylation system. Bottoms from the rerun column comprise the acid soluble oil (ASO) stream, which must be processed further so that the ASO stream can be disposed of without endangering the ecology.

Accordingly, an object of this invention is to provide a process for producing high octane alkylated hydrocarbons.

It is another object of this invention is to reduce the cost of processes for alkylation of an isoparaffin with an olefinic hydrocarbon to produce alkylate product.

A further object of this invention is to produce an improved method of separating contaminants from HF acid catalyst.

Other objects, aspects, as well as the several advantages of the invention will be apparent to those skilled in the art upon reading the specification, the drawing, and the appended claims.

SUMMARY OF THE INVENTION

Broadly, according to the invention, a stream comprising HF acid and acid soluble oil (ASO) is introduced into a stripping zone forming part of alkylation fractionation system, wherein HF is separated overhead for recycle and acid soluble oil stream is recovered as bottoms. Bottoms yield can be fractionated to recover low boiling paraffin and acid soluble oils.

In accordance with one embodiment of the invention, an acid soluble oil (ASO) stream is passed from the HF rerun column to the fractionation system's HF stripper with the bottoms of the stripper comprising propane plus acid-soluble oil along with a small portion of HF being charged to a propane deoiler. Bottoms from the propane deoiler comprise the ASO concentrate, which can be charged to storage. The processing of ASO through the HF stripper and the new propane deoiler produces an ASO concentrate which has negligible free HF therein and only traces of propane. This ASO concentrate is now suitable as cutting stock as for asphalt cements for admixing with fuel oil or as a specialty product such as a drying oil.

In accordance with another embodiment of the invention a slip stream of partially vaporized system HF catalyst containing acid soluble oils by-passes the conventional HF rerun column and is passed directly to the HF stripping column described in the preceding embodiment. The bottoms ASO-containing stream removed from the HF stripper is charged as in the previous embodiment to the new propane deoiler column.

DESCRIPTION OF THE DRAWING

The attached drawing illustrates an HF acid alkylation process incorporating a series of separation zones and acid recovery flows incorporating both embodiments of the invention.

Referring now to the drawing, olefin feed is introduced via line 1 into contact zone or alkylation zone 10 along with isoparaffin feed via line 2. Catalyst comprising makeup HF acid in line 3 and recycle acid in line 4 are introduced into contact zone 10 by way of line 5.

Figure 1:
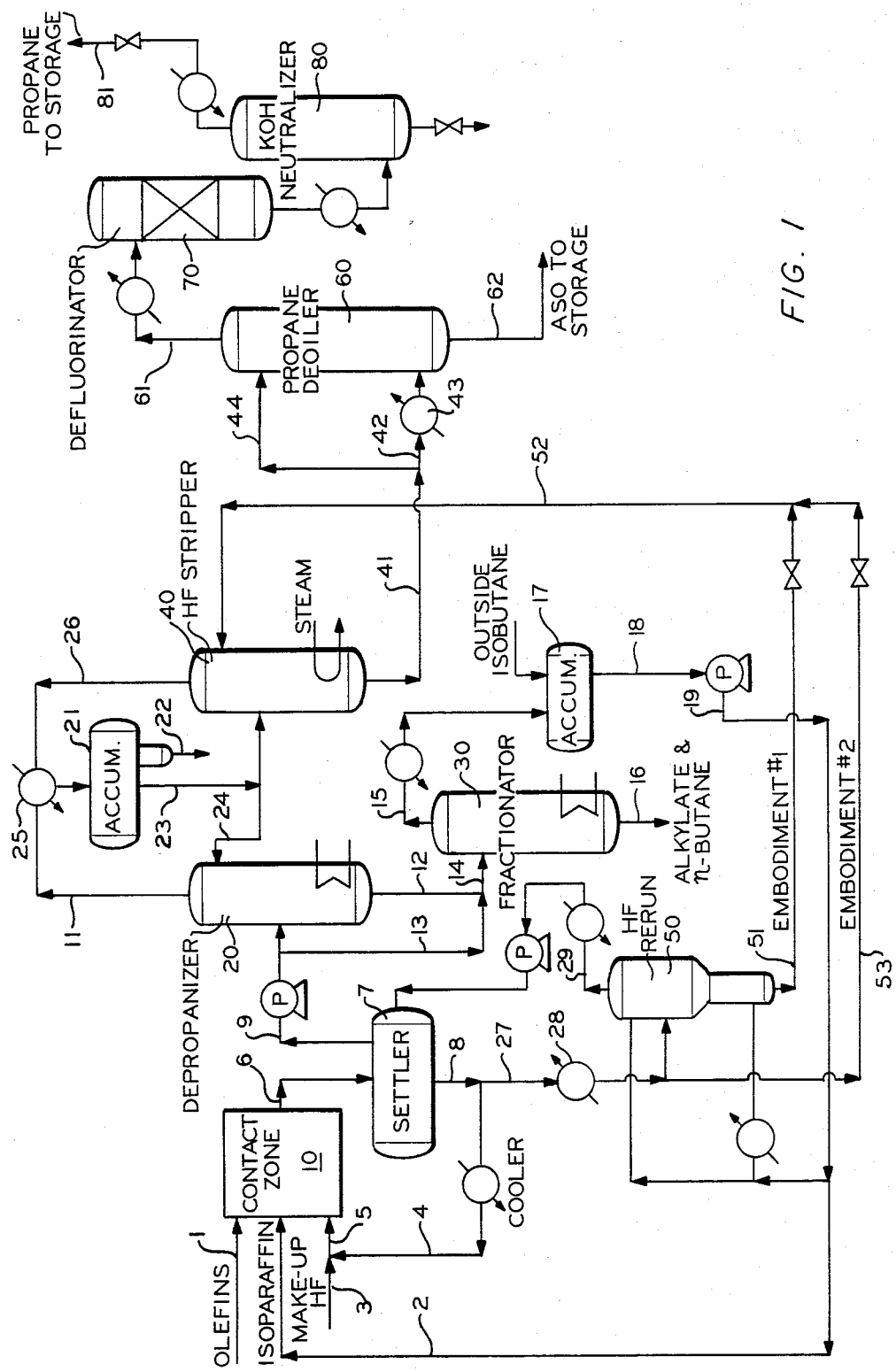

The isoparaffin to olefin mol ratio in reactor 10 can vary considerably but it generally is the range from about 2:1 up to about 25:1, usually from about 4:1 to about 15:1. The total hydrocarbon to HF catalyst volume ratio can vary considerably depending on the specific system, but the usual range is from about 1:10 to about 10:1. The HF alkylation reaction can be carried out in a wide temperature range usually in the range of about 0° F. ($-18°$ C.) to about 150° F. (66° C.) and at a pressure sufficient to maintain a liquid phase conditions. The lower the reaction temperature, the higher the octane number of the butylenes alkylate. Since it is less expensive to use the cooling water the normal reaction zone temperatures is about 90° F. (32° C.)

Any isoparaffin alone or in admixture with another isoparaffin is suitable for use with present invention including isobutane, isopentane and isohexane. Among olefins that can be used are propylene, butylenes, amylene and many others alone or in admixture with other olefins. The invention is particularly suitable for the alkylation of isobutane with propylene and butylene.

The alkylation process can be carried out as a batch or a continuous operation although continuous operation is preferred for economic reasons. The alkylation reaction mixture is removed from zone 10 by way of line 6 and passed to settler 7 wherein the mixture is separated into an upper liquid hydrocarbon phase and a lower liquid HF acid phase which can be withdrawn from settler 7 via line 8.

The hydrocarbon phase separated in settler 7 is passed by way of line 9 to depropanizer 20 operated at conditions such that a stream comprising HF acid and light paraffins is taken overhead by way of line 11 and a bottoms stream comprising heavier hydrocarbons is removed by way of line 12.

The usual temperature in the upper portion of depropanizer 20 will be in the range of 110° F. to about 120° F., the bottom temperature in the range of 220° F. to about 230° F. and a pressure of 260 psig to about 300 psig. A portion of the hydrocarbon in line 9 can be passed by way of lines 13 and 14 to fractionation zone 30 which can also be called an isostripper. Fractionation zone 30 is operated under conditions such that isoparaffins, specifically isobutane, is taken overhead by way of line 15 and a bottoms stream comprising normal butane and alkylate is removed by way of line 16 as product.

The drawing shows separate depropanizer 20 and isostripper/fractionator 30. It should be understood that a combination depropanizer-isostripper in a single tower can be used as is known to those versed in alkylation.

Isobutane removed overhead in line 15 is cooled to condense the isobutane and condensate formed is passed to accumulator 17. Recycle isobutane is withdrawn from accumulator 17 by way of line 18, 19, and 2 and passed to contact zone 10.

Overhead stream 11 comprising propane and lighter hydrocarbons and some HF removed from depropanizer 20 is cooled in condenser 25 and the condensate passed to accumulator 21. HF acid is removed from a lower portion of accumulator 21 by way of line 22 and can be recycled as makeup HF in line 3 for introduction into contact zone 10. The hydrocarbon condensate in accumulator 21 is removed by line 23 and a portion is returned as reflux to an upper portion of column 20 by way of line 24 and the remainder is passed as feed to HF stripper 40. HF stripper 40 is operated under condition such that HF acid is taken overhead by way of line 26 and passed through condenser 25 and combined with the overhead from depropanizer 20 in accumulator 21.

In embodiment 1 of the invention an HF rerun column 50 is provided as part of the process. A slip stream comprising HF acid and acid-soluble oils is passed by way of line 27 through heater 28 and introduced into HF rerun column 50. HF rerun column 50 is operated under conditions such that HF acid is taken overhead by way of line 29 and returned to settler 7. A bottoms stream comprising acid-soluble oils and some HF acid is passed by line 51 to HF stripper 40. As indicated previously, HF stripper 40 is operated under conditions such that HF acid is taken overhead by way of line 26 and acid soluble oils and hydrocarbon, for example, propane, are removed as bottoms by way line 41 and passed to propane deoiler 60.

In embodiment 2 of the invention HF acid slip stream 27 by-passes HF rerun 50 and is passed directly by way of line 53 and 52 to HF stripper 40 separated as described above.

Propane stripper 40 will be operated under conditions to take overhead as vapor substantially all of the HF remained in the feed to the stripper and ASO plus propane as bottoms which will be operated under top temperature in the range of about 125° F. to about 130° F., a bottom temperature in the range of about 135° F. to about 145° F. and a pressure in the range of 295 psig to about 305 psig.

Bottoms stream 41 is passed in part via line 44 to an upper portion of propane deoiler 60 and the remainder passed through heater 43 and then introduced into a lower portion of deoiler 60. Stream 44 is introduced into an upper portion of deoiler 60 to knock down ASO so that it can be removed from a lower portion of deoiler 60 by way of line 62 for further handling as desired. Overhead stream 61 comprising propane is passed to defluorination zone 70 and then through KOH neutralizer 80 to remove impurities. The main propane product stream is removed by way of line 81.

DETAILED DESCRIPTION OF THE INVENTION

Using the process of the invention shown in the drawing, the following flow rates and the following operating conditions in specific units of the system are presented.

| Typical Operation (Embodiment #1) | | |
|---|---|---|
| Operating Conditions: | | |
| Alkylation Reactor (10): | | |
| Temperature, °F., | | 90 |
| Pressure, PSIA., | | 175 |
| IC$_4$/Olefin Liq. Vol. Ratio | | 12 to 1 |
| HF/Total Hydrocarbon Vol. Ratio | | 4 to 1 |
| Depropanizer (20): | | |
| Temperature, °F., | | |
| Top | | 116 |
| Bottom | | 225 |
| Pressure, PSIA. | | |
| Top | | 275 |
| Bottom | | 282 |
| Isostripper (30): | | |
| Temperature, °F., | | |
| Top | | 125 |
| Bottom | | 226 |
| Pressure, PSIA, | | |
| Top | | 98 |
| Bottom | | 105 |
| HF Stripper (40): | | |
| Temperature, °F., | | |
| Top | | 127 |
| Bottom | | 140 |
| Pressure, PSIA | | |
| Top | | 297 |
| Bottom | | 300 |
| HF Rerun Tower (50): | | |
| Temperature, °F., | | |
| Top | | 265 |
| Bottom | | 315 |
| Pressure, PSIA, | | |
| Top | | 119 |
| Bottom | | 120 |
| New Propane Deoiler (60): | | |
| Specific | Temperature, °F., | Ranges |
| 139 | Top | 124–154 |
| 145 | Bottom | 125–155 |
| Specific | Pressure, PSIA | |
| 287 | Top | 250–350 |
| 290 | Bottom | 253–355 |
| Defluorination Column (70): | | |
| Temperature, °F., (Vapor) | | 400 |
| Pressure (Inlet), PSIA | | 285 |
| Contains activated alumina or bauxite. | | |
| KOH Neutralizer (80): | | |
| Temperature °F., | | 95 |
| Pressure, PSIA | | 250 |

In an alkylation plant producing 1,600 barrels per day of alkylate, the usual quantity of ASO from the rerun column is about 50 gallons per day. The propane deoiler 60 contains at least 10, more preferably at least 15, fractionation trays. The diameter of this deoiler 60 is about two feet. Tray spacing is about two feet. The material of construction is monel-lined or monel-clad steel.

Stream 41, the liquid bottoms from HF stripper 40, is charged, in part, via conduit 42 to vaporizer 43 and into the bottom portion of propane deoiler 60. The remainder of liquid stream 41 is passed directly via conduit 44 into the upper portion of propane deoiler 60 to knock back any entrained ASO trying to pass overhead in propane vapor 61. The liquid volume ratio of stream 42 to 44 is usually about 10 to 1, but the amount of liquid 44 is adjustable inorder to knock back ASO in this portion of the deoiler 60 and maintain propane product purity via conduit 61. The acid soluble oil concentrate is recovered by way of conduit 62. The propane, as shown, is treated in defluorination 70 and KOH tower 80, and removed as "LPG Propane" at 81.

The HF content of ASO in line 51 from rerun column 50 ranges from 2 to 50 weight percent HF. The HF content of the ASO concentrate in stream 62 runs less than about 100 parts per million by weight of HF (less than about 0.01%).

In embodiment 2, wherein the HF rerun column 50 is by-passed, the HF catalyst slip-stream is passed via conduit 53 to the HF stripper 40. The operating conditions in the columns of the drawings are as in embodiment 1.

That which is claimed is:

1. A process for the acid-catalyzed alkylation of an isoparaffin with an olefin to produce an alkylate product which comprises the steps of
    (a) reacting an isoparaffin with an olefin in the presence of hydrogen fluoride alkylation catalyst in a reaction zone,
    (b) separating a hydrocarbon phase and a catalyst phase comprising HF acid and acid soluble oils (ASO) from step (a),
    (c) passing said hydrocarbon phase to a fractionation zone operated at conditions selected to separate a vaporous overhead stream comprising HF acid and light paraffins, and a bottoms stream comprising alkylate product,
    (d) cooling and condensing said vaporous overhead and separating the condensate formed into a hydrocarbon phase and a HF acid phase which can be recycled to said reaction zone in (a),
    (e) passing at least a portion of said hydrocarbon phase in (d) as reflux to said fractionation in (c) and the remainder to HF acid stripping zone operated at conditions selected to withdraw overhead a stream comprising HF acid and a bottoms stream comprising light paraffin and acid soluble oils (ASO),
    (f) separating said bottoms stream in (e) into a light paraffin stream and an acid soluble oils stream (ASO), and
    (g) passing at least a potion of said catalyst phase in (b) as a portion of the feed to said HF-acid stripping zone in (e).

2. A process according to claim 1 wherein said acid catalyst phase in (b) is passed to a separation zone operated at conditions to withdraw an overhead stream comprising hydrocarbon and soluble HF acid, and a bottoms stream comprising HF acid and acid soluble oils (ASO) which is passed as a portion of the feed to said HF-acid stripping zone in (e).

3. A process according to claim 1 wherein a portion of said catalyst phase in (b) is recycled to said reaction zone in (a) and the remainder is passed directly to said HF-acid stripping zone in (e).

4. A process according to claim 3 wherein at least a portion of said remainder removed in (b) is passed to an HF rerun separation zone operated at conditions to withdraw an overhead stream comprising HF acid which is returned to said separation in (b), and a stream comprising HF acid and acid soluble oils (ASO) which is passed to said HF acid stripping zone in (e).

5. A process according to claim 1 wherein said fractionation in (c) comprises two fractionation zones wherein at least a portion of said hydrocarbon phase in (b) is passed as feed to a first fractionation zone operated at conditions to withdraw overhead a vaporous stream comprising HF and light paraffins and a bottoms stream comprising heavier hydrocarbons, which is combined with the remainder of said hydrocarbon phase as feed for the second fractionation zone operated at conditions to withdraw isoparaffin overhead and alkylate as bottoms.

6. A process according to claim 1 further characterized in that said isoparaffin contains from about 4 to about 7 carbon atoms/molecule and said olefin contains from about 3 to about 7 carbon atoms/molecule.

7. A process according to claim 1 wherein the isoparaffin-olefin admixture in (a) is formed from isobutane and an olefin having from 3 to 5 carbon atoms per molecule.

8. A process according to claim 5 wherein said acid catalyst phase in (b) is passed to a separation zone operated at conditions to withdraw an overhead stream comprising HF acid and entrained hydrocarbons and a bottoms stream comprising HF acid and acid soluble oils (ASO) which is passed as a portion of the feed to said HF-acid stripping zone in (e).

9. A process according to claim 5 wherein a portion of said catalyst phase in (b) is recycled to said reaction zone in (a) and the remainder is passed directly to said HF-acid stripping zone in (e).

10. A process according to claim 9 wherein said remainder is passed to a separation zone operated at conditions to withdraw an overhead stream comprising HF acid and a bottoms stream comprising HF acid and acid soluble oils (ASO) which is passed to HF-acid stripping zone in (e).

* * * * *

UNITED STATES PATENT AND TRADEMARK OFFICE
CERTIFICATE OF CORRECTION

PATENT NO. : 4,513,165
DATED : April 23, 1985
INVENTOR(S) : Joe Van Pool

It is certified that error appears in the above-identified patent and that said Letters Patent is hereby corrected as shown below:

On the title page;
Assignee should be: Phillips Petroleum Company
Bartlesville, Oklahoma Signed and Sealed this Thirteenth Day of August 1985

[SEAL]

Attest:

DONALD J. QUIGG

Attesting Officer

Acting Commissioner of Patents and Trademarks